(12) United States Patent
Taniguchi et al.

(10) Patent No.: US 8,815,074 B2
(45) Date of Patent: Aug. 26, 2014

(54) METHOD FOR REDUCING CARBON DIOXIDE

(71) Applicant: Panasonic Corporation, Osaka (JP)

(72) Inventors: Reiko Taniguchi, Osaka (JP); Satoshi Yotsuhashi, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/872,638

(22) Filed: Apr. 29, 2013

(65) Prior Publication Data

US 2013/0306488 A1 Nov. 21, 2013

Related U.S. Application Data

(63) Continuation of application No. PCT/JP2012/003502, filed on May 29, 2012.

(30) Foreign Application Priority Data

Aug. 29, 2011 (JP) .................................. 2011-185493

(51) Int. Cl.
C25B 1/00 (2006.01)
C25B 3/00 (2006.01)
C25B 3/10 (2006.01)
C07C 53/02 (2006.01)
C25B 3/04 (2006.01)
B01J 27/04 (2006.01)
C25B 9/08 (2006.01)
C25B 3/02 (2006.01)

(52) U.S. Cl.
CPC ... *C25B 3/04* (2013.01); *C25B 3/10* (2013.01); *C25B 3/02* (2013.01); *C25B 1/00* (2013.01); *C25B 3/00* (2013.01); *C07C 53/02* (2013.01); *B01J 27/04* (2013.01); *C25B 9/08* (2013.01)
USPC ............ 205/440; 205/415; 205/462; 205/555

(58) Field of Classification Search
CPC .............. C25B 1/00; C25B 3/00; C25B 3/02; C25B 3/04; C25B 3/10; C07C 53/02
USPC ................................... 205/415, 440, 462, 555
See application file for complete search history.

(56) References Cited

U.S. PATENT DOCUMENTS 4,921,585 A 5/1990 Molter
5,234,768 A 8/1993 Furuya
(Continued)

FOREIGN PATENT DOCUMENTS

JP 58-057267 A 4/1983
JP 64-015388 A 1/1989
(Continued)

OTHER PUBLICATIONS

International Search Report issued in International Patent Application No. PCT/JP2012/003502 mailed on Aug. 28, 2012.
(Continued)

*Primary Examiner* — Edna Wong
(74) *Attorney, Agent, or Firm* — McDermott Will & Emery LLP

(57) ABSTRACT

A method for reducing carbon dioxide with use of a device for reducing carbon dioxide includes steps of (a) preparing the device. The device includes a vessel, a cathode electrode and an anode electrode. An electrolytic solution is stored in the vessel, the cathode electrode contains a copper rubeanate metal organic framework, the copper rubeanate metal organic framework is in contact with the electrolytic solution, the anode electrode is in contact with the electrolytic solution, and the electrolytic solution contains carbon dioxide. The method further includes step of (b) applying a voltage difference between the cathode electrode and the anode electrode so as to reduce the carbon dioxide.

12 Claims, 2 Drawing Sheets

(56) References Cited

U.S. PATENT DOCUMENTS

| | | |
|---|---|---|
| 5,284,563 A | 2/1994 | Fujihira et al. |
| 2009/0062110 A1 | 3/2009 | Koshino et al. |
| 2012/0018311 A1 | 1/2012 | Yotsuhashi et al. |

FOREIGN PATENT DOCUMENTS

| | | | | |
|---|---|---|---|---|
| JP | 1-205088 A | | 8/1989 | |
| JP | 01-313313 A | | 12/1989 | |
| JP | 2-15186 A | | 1/1990 | |
| JP | 3-111587 A | | 5/1991 | |
| JP | 4-013880 A | | 1/1992 | |
| JP | 5-074458 A | | 3/1993 | |
| JP | 2004031174 A | * | 1/2004 | .............. H01M 4/86 |
| JP | 3675793 B2 | | 7/2005 | |
| JP | 2006-063050 A | | 3/2006 | |
| JP | 2007-238601 A | | 9/2007 | |
| JP | 4000562 B2 | | 10/2007 | |
| JP | 4129763 B2 | | 8/2008 | |
| JP | 4167775 B2 | | 10/2008 | |
| JP | 04-329888 B2 | | 9/2009 | |
| JP | 2011-082144 A | | 4/2011 | |
| JP | 4724783 B1 | | 4/2011 | |

OTHER PUBLICATIONS

Proceedings (II) of the 92nd Spring Meeting of the Chemical Society of Japan w/ English abstract, p. 433, 2 F2-47, 2012.

Chemistry Letters, pp. 1695-1698, 1985.

Yamamoto, "Research Completion Report" and it's partial English translation, Japan Science and Technology Agency, 2008.

* cited by examiner

METHOD FOR REDUCING CARBON DIOXIDE

This application is a Continuation of PCT/JP2012/003502 filed on May 29, 2012, which claims foreign priority of Japanese Patent Application No. 2011-185493 filed on Aug. 29, 2011, the entire contents of both of which are incorporated herein by reference.

TECHNICAL FIELD

The present disclosure relates to a method for reducing carbon dioxide.

SUMMARY

One of the purposes of the present disclosure is to provide a novel method for reducing carbon dioxide.

According to one aspect of the present disclosure, a method for reducing carbon dioxide with use of a device for reducing carbon dioxide includes the following steps (a) and (b). In step (a), the device for reducing carbon dioxide is prepared. The device includes a vessel, a cathode electrode, and an anode electrode. An electrolytic solution is stored in the vessel. The cathode electrode contains a copper rubeanate metal organic framework, and the copper rubeanate metal organic framework is in contact with the electrolytic solution. The anode electrode is in contact with the electrolytic solution, and the electrolytic solution contains carbon dioxide. In step (b), a voltage difference is applied between the cathode electrode and the anode electrode so as to reduce the carbon dioxide.

In some embodiments, the vessel may include a solid electrolyte membrane. The solid electrolyte membrane may be interposed between the cathode electrode and the anode electrode.

In some embodiments, in the step (b), the voltage difference may be not less than 2 volts.

In some embodiments, in the step (b), the carbon dioxide may be reduced on the cathode electrode.

In some embodiments, in the step (b), formic acid may be generated on the cathode electrode.

According to another aspect of the present disclosure, a method for generating formic acid includes the following steps (a) and (b). In step (a), a device is prepared. The device includes a vessel, a cathode electrode, and an anode electrode. An electrolytic solution is stored in the vessel. The cathode electrode contains a copper rubeanate metal organic framework and the copper rubeanate metal organic framework is in contact with the electrolytic solution. The anode electrode is in contact with the electrolytic solution, and the electrolytic solution contains carbon dioxide. In step (b), a voltage is applied difference between the cathode electrode and the anode electrode so as to generate the formic acid.

In some embodiments, the vessel may comprise a solid electrolyte membrane. The solid electrolyte membrane may be interposed between the cathode electrode and the anode electrode.

In some embodiments, in the step (b), the voltage difference may be not less than 2 volts.

In some embodiments, in the step (b), the carbon dioxide may be reduced on the cathode electrode.

In some embodiments, in the step (b), the formic acid may be generated on the cathode electrode.

The present disclosure provides a novel method for reducing carbon dioxide. In particular, the disclosed method is efficient in producing formic acid.

DESCRIPTION OF EMBODIMENTS

The embodiment of the present disclosure is described below.

(Step (a))

In the step (a), a device 20 for reducing carbon dioxide is prepared.

Figure 1:
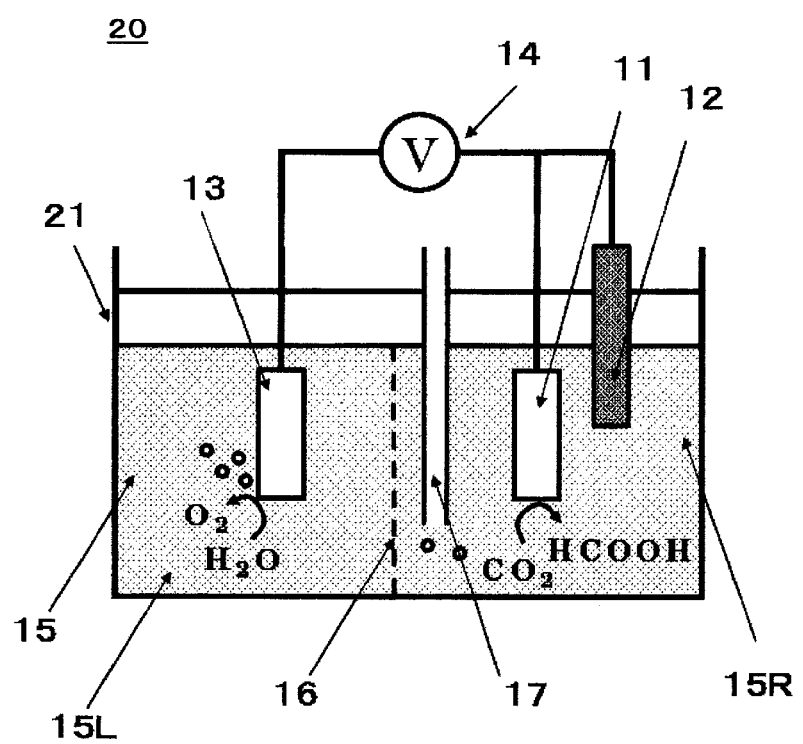
FIG. 1 shows an exemplary device for reducing carbon oxide according to the embodiment 1.
Figure 2:
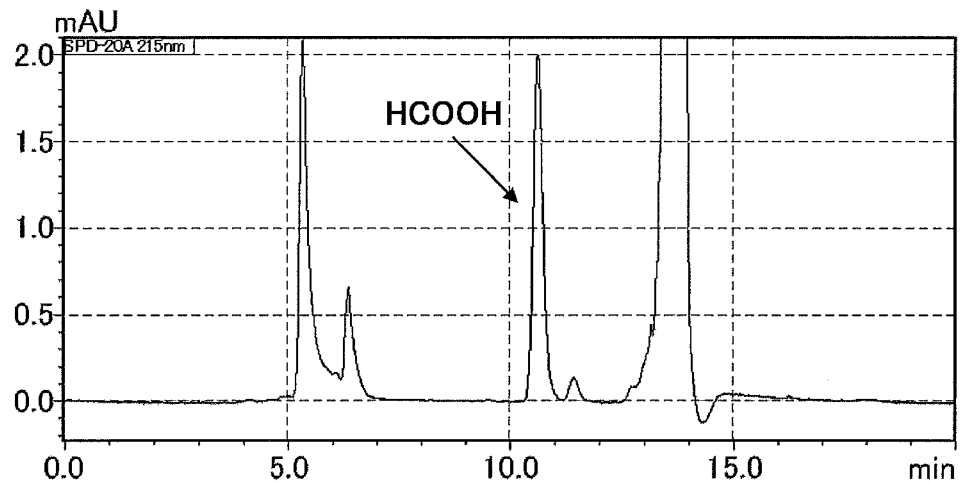
FIG. 2 shows a measurement result of the liquid chromatography according to the example 1A.
Figure 3:
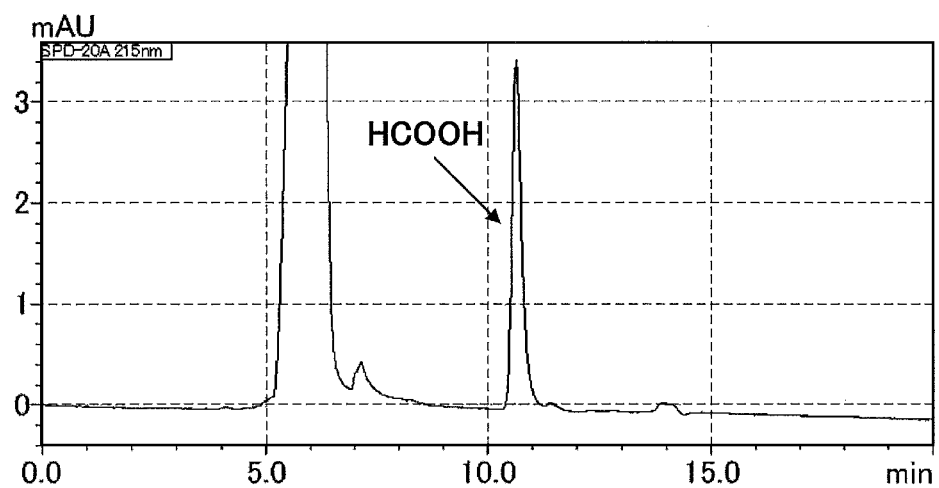
FIG. 3 shows a measurement result of the liquid chromatography according to the example 2A.

As shown in FIG. 1, the device 20 includes a vessel 21, a cathode electrode 11, and an anode electrode 13.

An electrolytic solution 15 is stored in the vessel 21. An example of the electrolytic solution 15 is a potassium bicarbonate aqueous solution or a potassium chloride aqueous solution. The electrolytic solution 15 contains carbon dioxide. It is preferable that the electrolytic solution 15 is weakly acidic in the state where carbon dioxide is dissolved in the electrolytic solution 15.

The cathode electrode 11 contains a copper rubeanate metal organic framework. The copper rubeanate metal organic framework may be found in Japanese laid-open patent application publication No. Hei 05-074458, and has the following molecular structure.

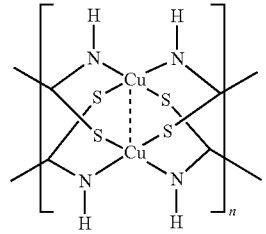

[Chem. 1]

An example of a method for preparing the cathode electrode 11 is described below.

First, a rubeanic acid solution is mixed to a solution containing copper ion to obtain precipitated particles each formed of copper rubeanate metal organic framework. The obtained particles each formed of copper rubeanate metal organic framework were dispersed in an organic solvent so as to obtain slurry. An example of the organic solvent is isopropyl alcohol.

Then, this slurry is applied to a conductive substrate to obtain a cathode electrode 11.

It is preferable that the conductive substrate has a shape of a film or a plate. An example of the conductive substrate is a carbon paper, a metal substrate, a glassy carbon substrate or a conductive silicon substrate.

The cathode electrode 11 is in contact with the electrolytic solution 15. To be more exact, the copper rubeanate metal organic framework included in the cathode electrode 11 is in contact with the electrolytic solution 15. In FIG. 1, the cathode electrode 11 is immersed in the electrolytic solution 15. Only a part of the cathode electrode 11 may be immersed in the electrolytic solution 15, as long as the copper rubeanate metal organic framework is in contact with the electrolytic solution 15.

The anode electrode 13 contains a conductive material. An example of the suitable conductive material is carbon, platinum, gold, silver, copper, titanium, or iridium oxide. The material of the conductive material is not limited, as long as the conductive material is not decomposed.

The anode electrode 13 is in contact with the electrolytic solution 15. To be more exact, the conductive material comprised in the anode electrode 13 is in contact with the electrolytic solution 15. In FIG. 1, the anode electrode 13 is immersed in the electrolytic solution 15. Only a part of the anode electrode 13 may be immersed in the electrolytic solution 15, as long as the conductive material is in contact with the electrolytic solution 15.

As shown in FIG. 1, it is preferable the vessel 21 includes a tube 17. Carbon dioxide is supplied to the electrolytic solution 15 through the tube 17. One end of the tube 17 is immersed in the electrolytic solution 15.

It is preferable that a solid electrolyte membrane 16 is provided in the vessel 21. This reason is mentioned later in the step (b). An example of the solid electrolyte membrane 16 is a Nafion (registered trademark) film available from Du Pont Kabushiki Kaisha. Only protons can penetrate the solid electrolyte membrane 16.

The solid electrolyte membrane 16 is interposed between the cathode electrode 11 and the anode electrode 13. The solid electrolyte membrane 16 divides the electrolytic solution 15 into an anode liquid 15L and a cathode liquid 15R. The anode electrode 13 is in contact with the anode liquid 15L. The cathode electrode 11 is in contact with the cathode liquid 15R.

As shown in FIG. 1, it is preferable that a reference electrode 12 is provided. The reference electrode 12 is in contact with the electrolytic solution 15. When the solid electrolyte membrane 16 is used, the reference electrode 12 is in contact with the cathode liquid 15R. The reference electrode 12 is electrically connected to the cathode electrode 11. An example of the reference electrode 12 is a silver/silver chloride electrode.

(Step (b))

In the step (b), the voltage difference is applied between the cathode electrode 11 and the anode electrode 13. This causes carbon dioxide contained in the electrolytic solution 15 (to be more exact, the cathode liquid 15R) to be reduced on the cathode electrode 11. As a result, formic acid is produced on the cathode electrode 11.

Oxygen is produced by oxidizing water on the anode electrode 13. The solid electrolyte membrane 16 inhibits a reverse reaction which may occur on the anode electrode 13. In other words, if the formic acid generated on the cathode electrode 11 reaches the anode electrode 13, the formic acid would be oxidized on the anode electrode 13. As a result, the generated formic acid would return to carbon dioxide. The solid electrolyte membrane 16 inhibits this reverse reaction.

It is preferable that a potentiostat 14 is used to apply a voltage difference between the cathode electrode 11 and the anode electrode 13.

It is preferable that the voltage difference applied between the cathode electrode 11 and the anode electrode 13 is 2.0 volts or more.

Example 1A

Preparation of Cathode Electrode 11

A cathode electrode 11 according to the example 1 was prepared as below. Rubeanic acid used in the example 1 was purchased from Wako Pure Chemical Industries, Ltd.

An ethanol solution of rubeanic acid having a concentration of 50 mM and an aqueous solution of cupric sulfate having a concentration of 50 mM were mixed to prepare a mixture. A precipitation was observed in the mixture. The precipitation was separated by centrifuge. The precipitation was washed with ethanol and subsequently washed with distilled water. Finally, the precipitation was air-dried. Thus, particles each formed of copper rubeanate metal organic framework (hereinafter, referred to as "CR-MOF") were obtained. The CR-MOF particles had an average particle diameter of approximately 3 micrometers.

Then, these particles were dispersed in isopropyl alcohol to prepare slurry of CR-MOF.

The slurry of CR-MOF was dropped on a conductive carbon paper (hereinafter, referred to as "CP") having a thickness of 0.36 millimeters and air-dried. In this manner, the cathode electrode 11 according to the example 1 was prepared. The distribution density of the CR-MOF particles on the cathode electrode 11 is approximately $1 \times 10^7/cm^2$.

(Preparation of Device 20)

A device 20 shown in FIG. 1 was prepared with use of the cathode electrode 11 thus obtained. The vessel 21 had a volume of 230 milliliters. The reference electrode 12 and the anode electrode 13 were an Ag/AgCl electrode and a platinum wire electrode, respectively. An electrolytic solution 15 was a potassium bicarbonate ($KHCO_3$) aqueous solution having a concentration of 0.5M. In other words, both of the cathode liquid 15R and the anode liquid 15L were a potassium bicarbonate ($KHCO_3$) aqueous solution having a concentration of 0.5M. The amount of the electrolytic solution 15 was 140 milliliters. A solid electrolyte membrane 16 was purchased from Sigma-Aldrich Japan K.K. (trade name: Nafion (Registered trade mark) 117).

(Injection of Carbon Dioxide)

Carbon dioxide was injected by bubbling to the cathode liquid 15R at a flow rate of 200 milliliters/minute for thirty minutes through the tube 17. In this way, the carbon dioxide was saturated in the cathode liquid 15R. The vessel having a volume of 230 milliliters included a lid (not shown), and had the electrolytic solution 15 (liquid phase) of 140 milliliters and gaseous carbon dioxide (gas phase) having a volume of 90 milliliters. The device 20 was sealed by the lid.

(Reduction of Carbon Dioxide)

Voltages of −1.4 volts, 0 volts, and +1.2 volts were applied to the cathode electrode 11, the reference electrode 12, and the anode electrode 13, respectively. The current was 10 milli-amperes. This state was maintained for 1,000 seconds, namely 16 minutes 40 seconds. The total electric charge amount was 10 coulombs. Subsequently, a liquid phase component and a gas phase component were collected with use of syringes. The collected liquid phase component was analyzed with a liquid chromatography. The collected gas phase component was analyzed with a gas chromatography. The result is shown in Table 1.

Example 1B

An experiment similar to the example 1A was performed, except that a voltage of −1.5 volts was applied to the cathode electrode 11. The result is shown in Table 1.

Example 1C

An experiment similar to the example 1A was performed, except that a voltage of −1.6 volts was applied to the cathode electrode 11. The result is shown in Table 1.

Comparative Example 1A

An experiment similar to the example 1A was performed, except that the slurry of CR-MOF was not dropped on a carbon paper and a voltage of −1.8 volts was applied to the cathode electrode 11. In other words, in the comparative example 1, the cathode electrode 11 was formed of a carbon paper. The result is shown in Table 1.

Comparative Example 1B

An experiment similar to the example 1A was performed, except that a copper electrode was used as the cathode electrode 11 and a voltage of −1.8 volts was applied to the cathode electrode 11. The result is shown in Table 1.

Examples 2 and Comparative Examples 2

Experiments similar to the examples 1A and 1C and the comparative examples 1A and 1B were performed, except that a potassium chloride (KCl) aqueous solution having a concentration of 0.5M was used as the electrolytic solution 15 instead of the potassium bicarbonate ($KHCO_3$) aqueous solution. In the experiments similar to the comparative examples 1A and 1B, voltages applied to the cathode electrode 11 were different from those of the comparative examples 1A and 1B. The result is shown in Table 2.

Table 1 and Table 2 show amounts of formic acid, carbon monoxide, methane, ethylene, and ethane generated in the examples and the comparative examples.

TABLE 1

| Solution 0.5M $KHCO_3$ | Cathode | Electric Potential of electrolysis | amounts of the products [micro mol] | | | | | Selectivity of HCOOH |
|---|---|---|---|---|---|---|---|---|
| | | | HCOOH | CO | $CH_4$ | $C_2H_4$ | $C_2H_6$ | |
| Example 1A | CR-MOF | −1.4 V | 9.5 | 0.02 | 0.001 | 0.0001 | 0.0001 | 99.8% |
| Example 1B | CR-MOF | −1.5 V | 8.9 | 0.05 | 0.004 | 0.0003 | 0.0006 | 99.4% |
| Example 1C | CR-MOF | −1.6 V | 12.9 | 0.05 | 0.007 | 0.0004 | 0.0006 | 99.6% |
| Comparative Example 1A | CP | −1.8 V | 0.2 | 0.02 | 0.016 | 0.0007 | 0.0014 | 84.1% |
| Comparative Example 1B | Cu | −1.8 V | 13.7 | 0.21 | 0.64 | 0.047 | 0.0004 | 93.9% |

TABLE 2

| Solution 0.5M KCl | Cathode | Electric Potential of electrolysis | amounts of the products [micro mol] | | | | | Selectivity of HCOOH |
|---|---|---|---|---|---|---|---|---|
| | | | HCOOH | CO | $CH_4$ | $C_2H_4$ | $C_2H_6$ | |
| Example 2A | CR-MOF | −1.4 V | 11.3 | 0.07 | 0.01 | 0.002 | 0.003 | 99.2% |
| Example 2B | CR-MOF | −1.6 V | 22.3 | 0.22 | 0.02 | 0.003 | 0.003 | 98.9% |
| Comparative Example 2A | CP | −2.0 V | 2.6 | 0.26 | 0.04 | 0.001 | 0.001 | 89.8% |
| Comparative Example 2B | Cu | −1.6 V | 2.7 | 0.89 | 0.75 | 2.684 | 0.002 | 38.2% |

As is clear from Table 1 and Table 2, the carbon oxide is reduced to formic acid in the examples. The generation rate of formic acid according to the examples is higher than those according to the comparative examples.

INDUSTRIAL APPLICABILITY

The present disclosure provides a novel method for reducing carbon dioxide. In particular, the disclosed methods are efficient in producing formic acid.

What is claimed is:

1. A method for reducing carbon dioxide with use of a device for reducing carbon dioxide, the method comprising steps of:
   (a) preparing the device, wherein:
   the device comprises:
     a vessel;
     a cathode electrode; and
     an anode electrode,
   an electrolytic solution is stored in the vessel,
   the cathode electrode contains a copper rubeanate metal organic framework,
   the copper rubeanate metal organic framework is in contact with the electrolytic solution,
   the anode electrode is in contact with the electrolytic solution, and
   the electrolytic solution contains carbon dioxide; and
   (b) applying a voltage difference between the cathode electrode and the anode electrode so as to reduce the carbon dioxide.

2. The method according to claim 1, wherein:
   the vessel comprises a solid electrolyte membrane, and
   the solid electrolyte membrane is interposed between the cathode electrode and the anode electrode.

3. The method according to claim 1, wherein in the step (b), the voltage difference is not less than 2 volts.

4. The method according to claim 1, wherein in the step (b), the carbon dioxide is reduced on the cathode electrode.

5. The method according to claim 1, wherein in the step (b), formic acid is generated on the cathode electrode.

6. The method according to claim 1, wherein the copper rubeanate metal organic framework has the following molecular structure:

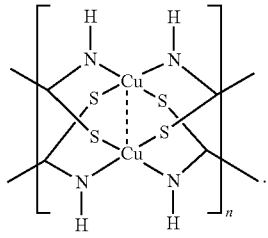

7. A method for generating formic acid, the method comprising steps of:
   (a) preparing a device, wherein:
   the device comprises:
     a vessel;
     a cathode electrode; and
     an anode electrode,
   an electrolytic solution is stored in the vessel,
   the cathode electrode contains a copper rubeanate metal organic framework,
   the copper rubeanate metal organic framework is in contact with the electrolytic solution,
   the anode electrode is in contact with the electrolytic solution,
   the electrolytic solution contains carbon dioxide; and
   (b) applying a voltage difference between the cathode electrode and the anode electrode so as to generate the formic acid.

8. The method according to claim 7, wherein:
   the vessel comprises a solid electrolyte membrane, and
   the solid electrolyte membrane is interposed between the cathode electrode and the anode electrode.

9. The method according to claim 7, wherein in the step (b), the voltage difference is not less than 2 volts.

10. The method according to claim 7, wherein in the step (b), the carbon dioxide is reduced on the cathode electrode.

11. The method according to claim 7, wherein in the step (b), the formic acid is generated on the cathode electrode.

12. The method according to claim 7, wherein the copper rubeanate metal organic framework has the following molecular structure:

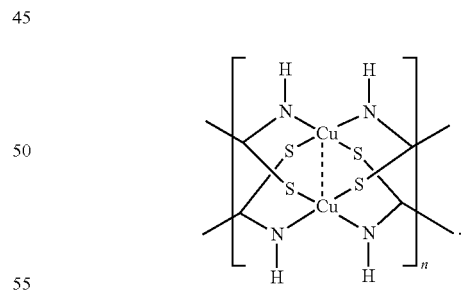

* * * * *